US008029495B2

(12) United States Patent
Pyles

(10) Patent No.: US 8,029,495 B2
(45) Date of Patent: Oct. 4, 2011

(54) INTRATHECAL CATHETER HAVING A STYLET WITH A CURVED TIP AND METHOD OF USE

(76) Inventor: Stephen T. Pyles, Ocala, FL (US)

(*) Notice: Subject to any disclaimer, the term of this patent is extended or adjusted under 35 U.S.C. 154(b) by 0 days.

(21) Appl. No.: 12/731,966

(22) Filed: Mar. 25, 2010

(65) Prior Publication Data

US 2010/0179509 A1 Jul. 15, 2010

Related U.S. Application Data

(62) Division of application No. 11/424,126, filed on Jun. 14, 2006, now abandoned.

(60) Provisional application No. 60/690,253, filed on Jun. 14, 2005.

(51) Int. Cl.
*A61M 31/00* (2006.01)

(52) U.S. Cl. ............... 604/510; 604/506; 604/95.04; 604/164.13; 604/170.01; 604/170.02; 604/170.03

(58) Field of Classification Search .............. 604/506, 604/510, 511, 512, 513, 164.13, 170.01, 604/170.02, 170.03
See application file for complete search history.

(56) References Cited

U.S. PATENT DOCUMENTS

| 2,118,631 | A | | 5/1938 | Charles |
| 3,128,769 | A | | 4/1964 | Scislowicz |
| 3,867,945 | A | | 2/1975 | Long |
| 4,811,743 | A | | 3/1989 | Stevens |
| 4,813,929 | A | | 3/1989 | Semrad |
| 4,813,938 | A | | 3/1989 | Raulerson |
| 4,834,709 | A | | 5/1989 | Banning et al. |
| 5,003,989 | A | | 4/1991 | Taylor et al. |
| 5,045,065 | A | | 9/1991 | Raulerson |
| 5,250,038 | A | | 10/1993 | Melker et al. |
| 5,304,140 | A | | 4/1994 | Kugo et al. |
| 5,484,419 | A | | 1/1996 | Fleck |
| 5,807,324 | A | * | 9/1998 | Griffin, III ................ 604/529 |
| 6,477,402 | B1 | | 11/2002 | Lynch et al. |
| 6,512,957 | B1 | | 1/2003 | Witte |
| 2004/0073197 | A1 | * | 4/2004 | Kim ............................ 604/891.1 |
| 2004/0220543 | A1 | * | 11/2004 | Heruth et al. ............. 604/506 |
| 2005/0107861 | A1 | | 5/2005 | Harris et al. |

OTHER PUBLICATIONS

Konstantin V. Slavin, MD; "Intramedullary Placement of Intrathecal Catheter. Report of a Rare Complication of Intrathecal Therapy;" International Neuromodulation Society, Neuromodulation, vol. 9, No. 2, 2006 94-99.
Medtronic, "Low Complication Catheter Implant Technique." Medtronic Intrathecal Catheter Model 8731, Feb. 2003. 17 pages.

(Continued)

*Primary Examiner* — Bhisma Mehta
(74) *Attorney, Agent, or Firm* — Gardner Groff Greenwald & Villanueva

(57) ABSTRACT

An apparatus includes a catheter for an intrathecal drug delivery system and a stylet having a curved forward end. Preferably, the curved forward end has a shape in the form of a "J" or a "C." Also preferably, the catheter has a distal end that conforms to the curved forward end of the stylet. Thus, the present invention provides a catheter having a blunt forward end that minimizes the risk of penetrating the substance of the spinal cord. Additionally, the curved forward end of the stylet can be formed of a springy material so that it straightens out during the processes of insertion through a guide needle and retraction from the needle.

7 Claims, 4 Drawing Sheets

OTHER PUBLICATIONS

Harney,D. and Victor,R., Traumatic Syrinx After Implantation of an Intrathecal Catheter; Regional Anesthesia and Pain Medicine, vol. 29, No. 6 Nov.-Dec. 2004; pp. 606-609.

Arrow International, Inc.; Product List: United States; Arrow CVC System; 2005; pp. 1-8.

Arrow International, Inc.; description of product No. AK-11142-B; http://www.arrowintl.com/products/boms/AK11142B.asp?cat=7&item=AK-11142-B&xsec=I-9-12; printed on Nov. 15, 2006, 2 pages.

Tripathi et al.; Direction of the J-Tip of the Guidewire, in Seldinger Technique, Is a Significant Factor in Misplacement of Subclavian Vein Catheter: A Randomized, Controlled Study; Anesth Analg; 2005; pp. 21-24; vol. 100; the International Anesthesia Research Society.

\* cited by examiner

INTRATHECAL CATHETER HAVING A STYLET WITH A CURVED TIP AND METHOD OF USE

CROSS REFERENCE TO RELATED APPLICATIONS

This application is a divisional of U.S. patent application Ser. No. 11/424,126, filed Jun. 14, 2006, now abanoned which claims priority to U.S. Provisional Patent Application Ser. No. 60/690,253, filed Jun. 14, 2005. The disclosures of application Ser. Nos. 11/424,126 and 60/690,253 are hereby incorporated herein by reference in their entireties for all purposes.

TECHNICAL FIELD

The present invention relates generally to the field of surgical instruments and methods, and more particularly to an intrathecal catheter having a stylet with a curved forward end.

BACKGROUND OF THE INVENTION

Human and animal subjects suffering from chronic pain have several options available to help alleviate the pain. One option is intrathecal drug delivery, in which a low dose of a medication, typically a narcotic such as morphine, is delivered to the intrathecal space (i.e., within the spinal canal). A typical system for intrathecal drug delivery includes a drug delivery pump implanted in the patient's abdomen, which has a reservoir for the medication, and a catheter leading from the pump into the intrathecal space. The pump releases the medication at a set rate, and the medication flows from the pump, through the catheter to the site of delivery in the intrathecal space. Intrathecal drug delivery is beneficial because typically smaller doses of the medication can be used, as compared to the dosages of those same medications taken orally.

However, implanting the device is not without risk. Inadvertently implanting the catheter into the spinal cord can result in permanent injury to the spinal cord, potentially resulting in irreversible paralysis. For example, there is some risk that the practitioner, when placing the guide needle or the styletted catheter within the spinal canal, might puncture the spinal cord with the sharp tip of the guide needle and/or the styletted catheter and subsequently accidentally thread the styletted catheter into the substance of the spinal cord. And since typically, most practitioners choose to perform this operation under general anesthesia in which the patient is completely unaware of the procedure, the patient will not know something is wrong until he or she wakes up, and in a more egregious case, the patient may wake up paralyzed from the waist down.

Therefore, a need exists for an apparatus and method that allows a catheter for an intrathecal drug delivery system to be guided more safely into proper placement within the intrathecal space.

SUMMARY OF THE INVENTION

Advantageously, the present invention provides an intrathecal catheter having a curved forward end for placement in the intrathecal space. The intrathecal catheter includes a guide wire or a stylet, within the catheter, that has a curved tip, and the tip of the catheter itself conforms to the shape of the stylet tip. Thus, the catheter provides a blunt forward end, which minimizes the likelihood of puncturing tissue, such as the spinal cord.

In an example form, the present invention provides an apparatus including a catheter for an intrathecal drug delivery system and a stylet, wherein the stylet has a curved forward end. Thus, the catheter has a tip that can conform to the curved forward end of the stylet. Preferably, the curved forward end of the stylet is in the shape of a "J" or a "C." Also preferably, the curved forward end of the stylet is formed of a resilient and flexible material.

In one embodiment, the catheter has a single lumen for housing the stylet and for carrying a fluid from a fluid source to target tissue. Preferably, the catheter has a biocompatible body with at least one opening extending along the body near its distal end for drug delivery to target tissue.

In another form, the present invention provides a method for introducing a catheter for an intrathecal drug delivery system into the intrathecal space. The method includes the steps of inserting a stylet having a curved forward end into an intrathecal catheter; inserting the intrathecal catheter into an incision in the body; and guiding the intrathecal catheter into the intrathecal space by manipulation of the combination of the stylet and the catheter. The method can further include the steps of removing the stylet from the intrathecal catheter such that the catheter tip straightens out in the intrathecal space; anchoring the intrathecal catheter to adjacent tissue; and connecting the intrathecal catheter to a drug delivery pump.

In yet another example form, the present invention includes a kit for intrathecal drug delivery. The kit can include one or more of the following items packaged in a single kit: an intrathecal catheter, a stylet having a curved forward end, a drug delivery pump, a guide needle, an insertion device, a tunneling tool, and suturing supplies.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 3:
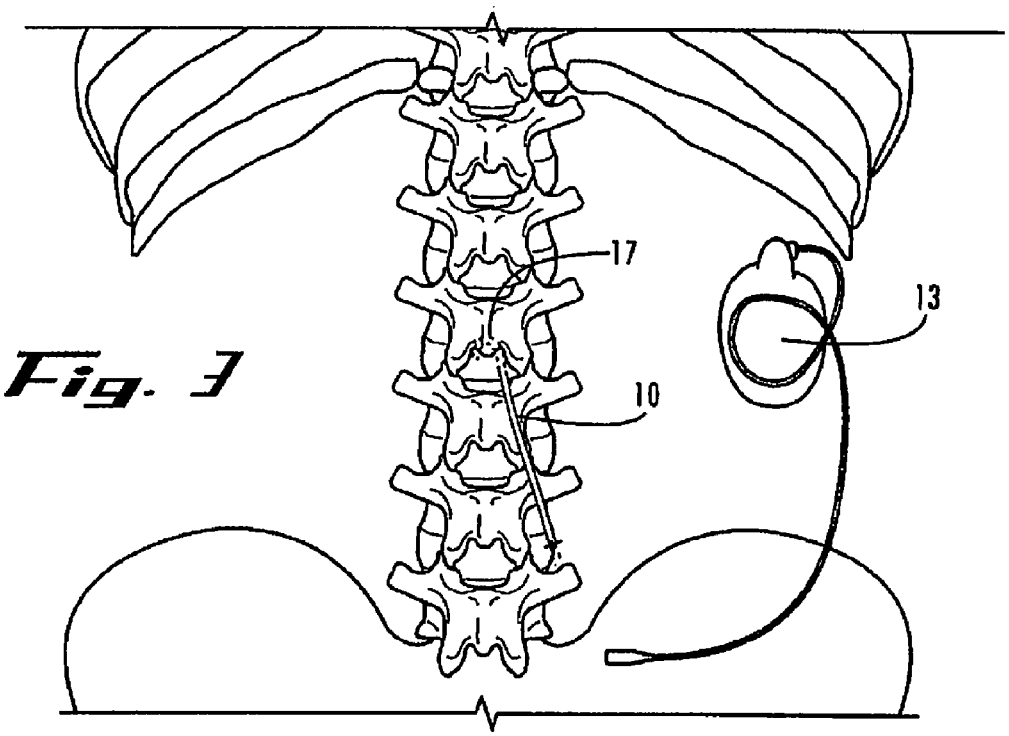
FIG. 3 depicts a pictorial representation of advancing the catheter of FIG. 1 through the intrathecal space.
Figure 4:
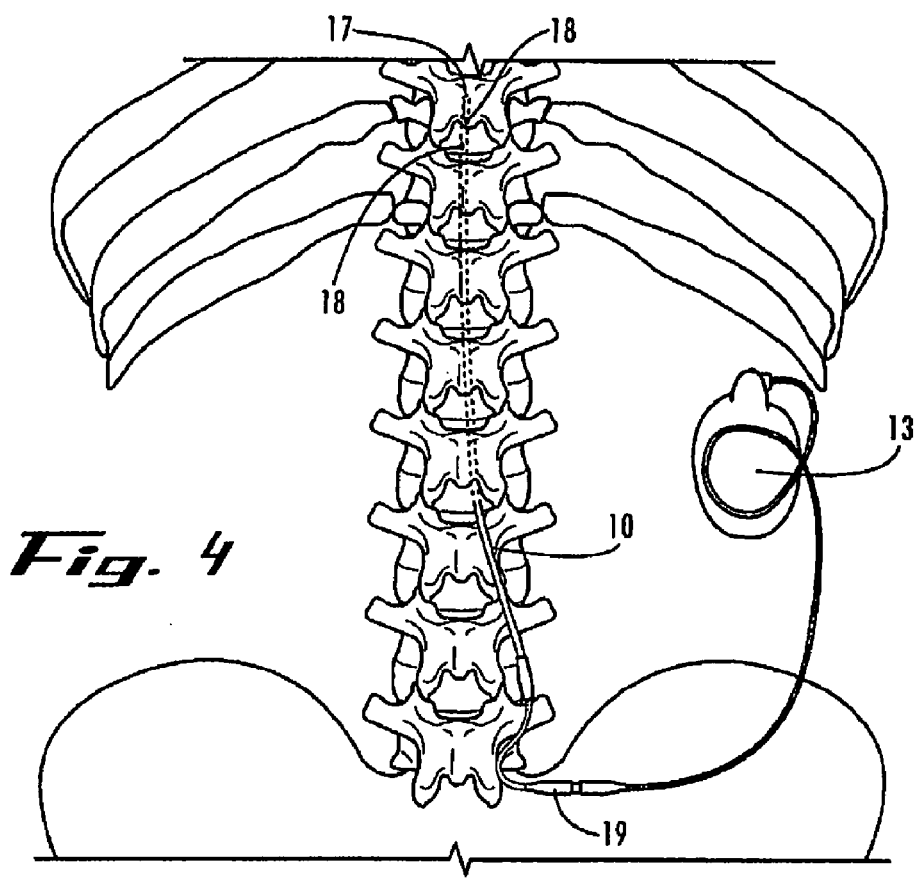
FIG. 4 depicts a pictorial representation of the catheter of FIG. 1 implanted in the intrathecal space.
Figure 5:
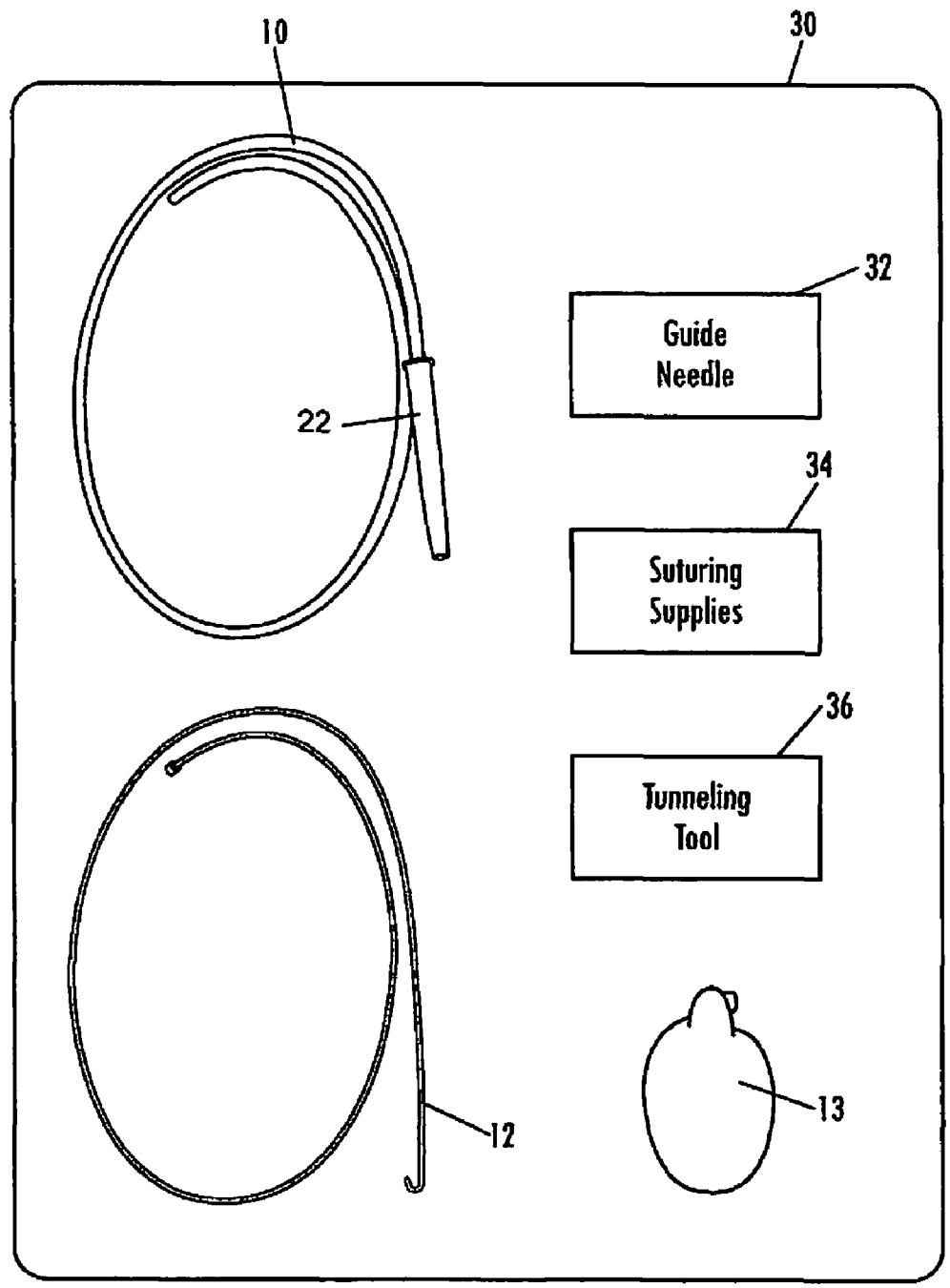
FIG. 5 depicts a representation of a kit comprising the catheter and stylet of FIG. 1.

Referring to FIGS. 1-4 a catheter 10 having an associated flexible stylet or guidewire 12 extending therethrough for an intrathecal drug delivery system is shown by way of an example embodiment. Intrathecal drug delivery systems, commonly referred to as morphine pumps, and methods of implanting such pumps are generally well known. Intrathecal drug delivery systems typically include a catheter 10 and a drug delivery pump 13, as shown in FIGS. 3 and 4. Referring back to FIGS. 1 and 2, the catheter 10 has a biocompatible body 14 constructed of a biocompatible and flexible material. Preferably, the body 14 has a single lumen or canal 16 extending therethrough for carrying a medication from the pump 13 to the intrathecal space and for housing the stylet 12. Alternatively, the catheter 10 can include dual lumens, one for carrying a medication and one for housing the stylet 12.

In an example embodiment, the catheter 10 has a length of about 60 to about 90 cm, an internal diameter in the range of about 0.4 to about 0.6 mm and more preferably in the range of 0.5 mm to 0.6 mm. In an example embodiment, the catheter 10 has an internal diameter of about 0.53 mm. The external diameter can be about 1.0 to about 3.0 mm, and more preferably from about 1.4 mm to about 2.0 mm, though those skilled in the art will understand that the dimensions can be larger or smaller. Preferably, the catheter 10 has a distal portion or tip 17 with a closed end 19. The distal portion 17 also preferably includes at least one and preferably a plurality of lateral (e.g., transverse to the catheter longitudinal axis) openings, slots, or holes 18 in the body 14 of catheter 10. The medication can be pumped through the lumen 16 forward to the distal portion 17 and then transversely out through the lateral openings and into the intrathecal space. As shown in the figures, the catheter 10 has three such openings 18, though those skilled in the art will understand that the catheter can have more or fewer openings. Those skilled in the art will also understand how to determine the placement of the openings and the spacing between the openings 18.

Also, a fitting 19, such as a conventional fitting as shown in FIG. 4, can be attached to the proximal end of the catheter 10 to connect to the drug delivery pump 13 implanted in the patient's abdomen once the stylet 12 has been removed.

Figure 1:
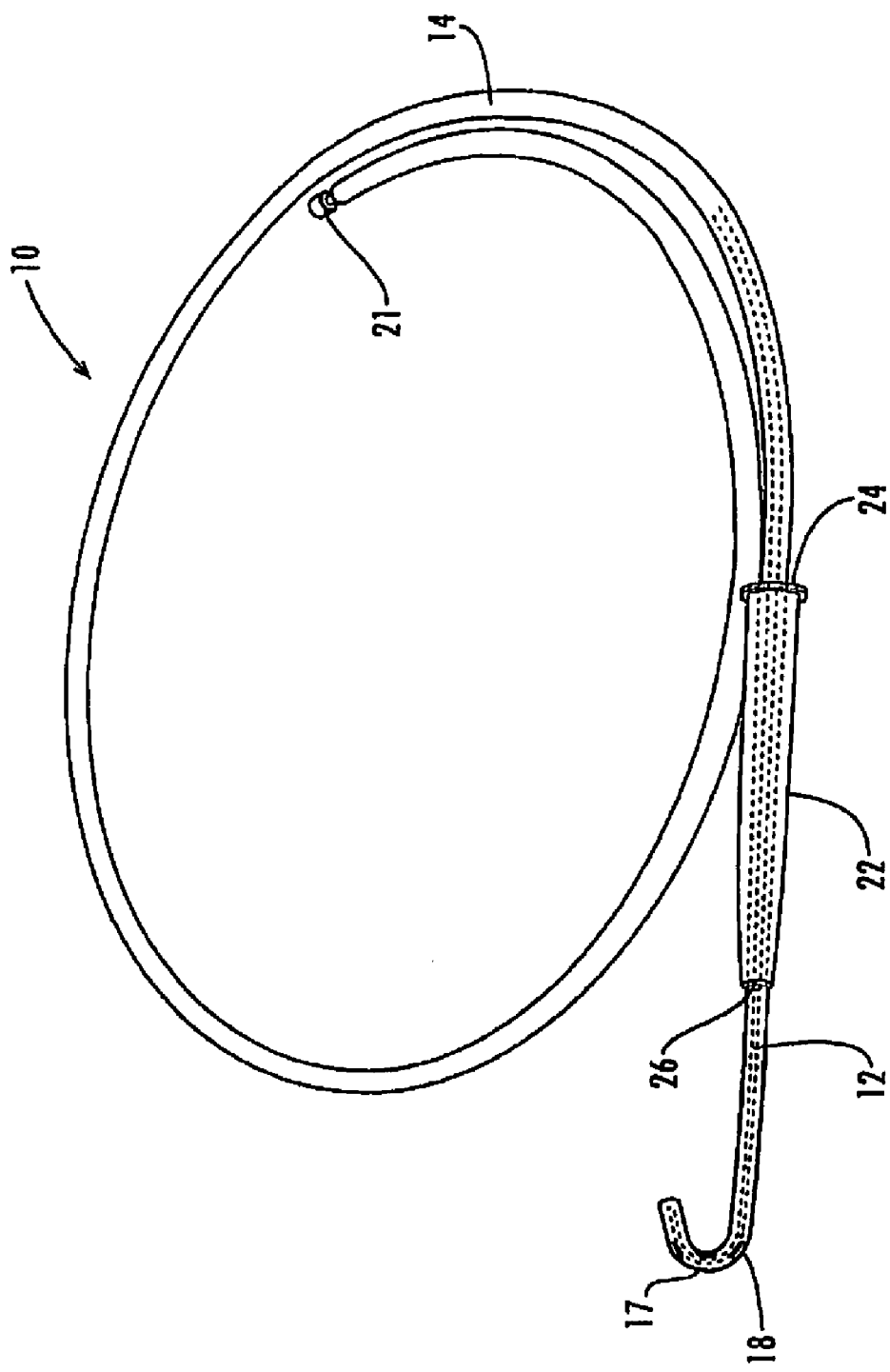
FIG. 1 depicts a perspective view of a catheter having a stylet with a curved forward tip according to an example embodiment of the present invention.
Figure 2:
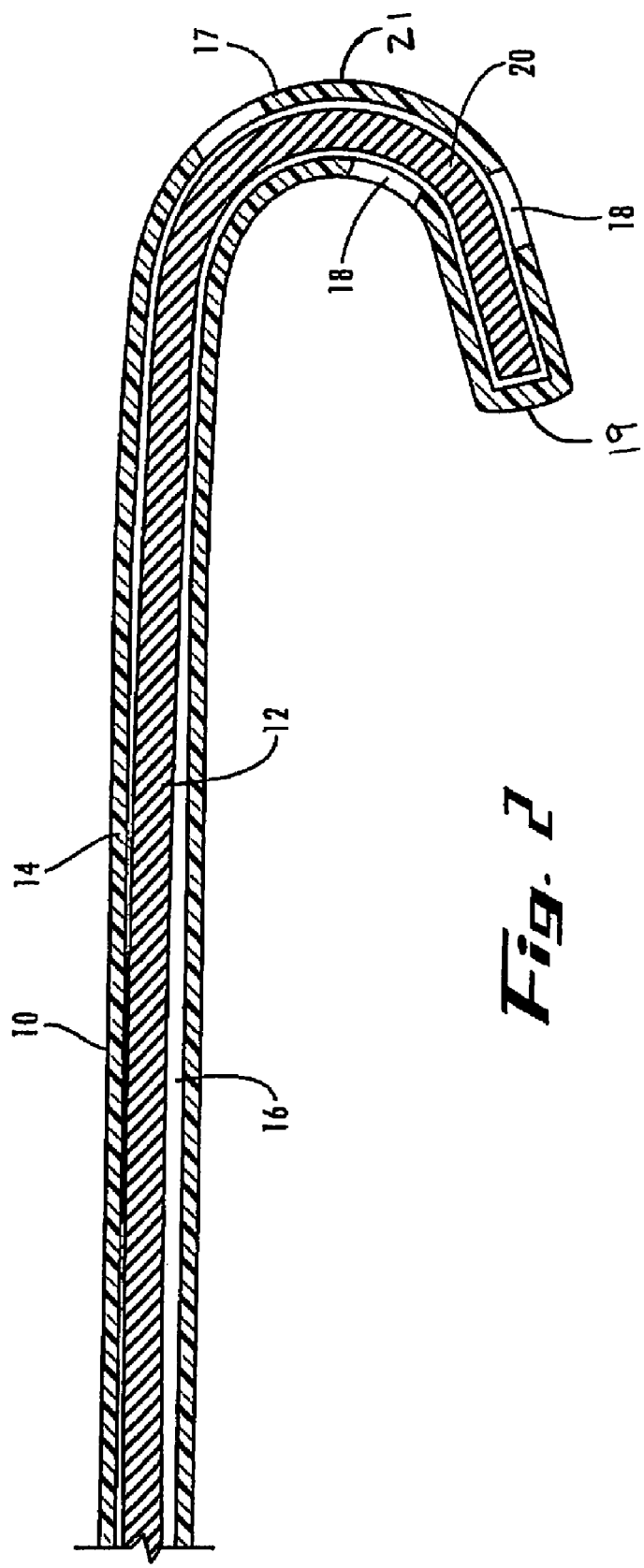
FIG. 2 depicts a longitudinal cross-sectional view of an end portion of the catheter of FIG. 1.

The stylet 12 has a tip or portion 20 at its distal end and a handle 21 at its proximal end for manipulating the stylet. Those skilled in the art will understand that the handle 21 shown in FIG. 1 is exemplary and that the handle can have a variety of shapes and sizes. Preferably, the tip 20 of the stylet 12 has the shape of a "J", a "C", or is otherwise curved, in its neutral state, such that a distal end thereof is bent beyond perpendicular (more than 90 degrees) relative to a longitudinal axis of a straight section of the stylet so as to provide a blunt leading portion 21 of the catheter distal portion 17, with a most-forward point along a mid-section of the curve, that will not puncture tissue as the stylet and associated surrounding intrathecal catheter 10 are guided through the intrathecal space (see FIG. 2). Thus, the distal portion 17 of the catheter 10 conforms to the shape of the distal tip 20 of the stylet 12 when the stylet is fully inserted into the catheter lumen 16 with the stylet distal tip positioned within the catheter distal portion adjacent its closed end (see FIG. 2). Thus, at no point in the catheter-insertion method does the distal tip 20 of the stylet 12 extend distally beyond the closed end 19 of the distal portion 17 of the catheter 10 (see FIGS. 1-4). Preferably, the tip 20 of the stylet 12 is stiffer or less flexible than the distal portion 17 of the catheter 10. By providing a blunt leading portion 21 of the catheter distal portion 17, the risk of puncturing tissue that otherwise should not be punctured is greatly minimized, as compared to using a sharp tip.

Preferably, the stylet 12 is constructed of a resilient and flexible material that allows the tip 20 to resiliently deflect and adjust from a curved position in its neutral state to a straight position when being inserted through a guide needle or when being retracted from the catheter 10. Thus, at least the curved tip 20 of the stylet 12 is springy or flexible in the sense that when the stylet is being retracted from the catheter 10, the curved tip of the stylet straightens out within the confines of the lumen 16 as it is being pulled therethrough, and with the stylet distal tip removed then the distal portion 17 of the catheter 10 is allowed to also straighten out, so that removal from the catheter is made easier and minimizes the chances of tearing the catheter. The tip 20 of the stylet 12 can be constructed of a spring or coil material. Additionally, the entire stylet 12 can be a unitary piece that is constructed of a resilient, flexible, and biocompatible material, such as a plastic or a metal. Upon removal from the catheter 10, the flexible distal tip 20 of the stylet 12 resiliently returns to its neutral curved shape.

The size of the stylet 12 can vary, but in an example embodiment, the diameter of the stylet is smaller than the internal diameter of the catheter 10 and is about 0.46 mm. Those skilled in the art will understand that the stylet 12 can have a larger or smaller diameter, such as in the range of about 0.2 mm to about 0.52 mm and more preferably in the range of about 0.4 mm to about 0.5 mm. The length of the stylet 12 is preferably similar to the length of the catheter 10, and can be about 38 cm to about 89 cm, though those skilled in the art will understand that the dimensions can be larger or smaller.

The practitioner inserts the catheter 10 with the stylet 12 through a guide needle previously inserted through an incision in the patient's back and into the intrathecal space. Those skilled in the art will understand where and how to insert the guide needle. To facilitate threading the styletted catheter 10 into the needle, an insertion device 22, as depicted in FIG. 1, can be used. The insertion device 22 is funnel-shaped, and has a larger distal end 24 through which the catheter 10 and stylet 12 are inserted, and a narrower forward end 26 which has an opening that can mate with the opening of the needle. Thus, the insertion device 22 facilitates threading the styletted catheter 10 through the needle by allowing the practitioner to insert the distal portion 17 of the catheter along with the tip 20 of the stylet into the insertion device. Alternatively, the styletted catheter 10 can be inserted through a guide needle having a flared proximal end. Also alternatively, the styletted catheter can be inserted through a stiff or rigid sheath. Additionally, the insertion device 22 or another generally funnel-shaped piece can be used to facilitate the threading of the stylet 12 into the catheter 10.

The guide needle or sheath generally deflects the curved tip 20 of the stylet 12 to at least a somewhat straight position so that the catheter and stylet can be threaded through the needle or sheath. Thus, while the styletted catheter 10 is threaded through he needle, the tip 20 of the stylet 12, and hence the distal portion 17 of the catheter 10, temporarily straighten out. Once the styletted catheter 10 is threaded through the needle, the tip 20 of the stylet 12 springs back into its curved shape (i.e., back to its neutral position), which causes the distal portion 17 of the catheter 10 to curve in shape. Alternatively, the curved tip of the catheter 10 can be threaded through a needle or sheath of a diameter sufficient to accommodate the diameter of the catheter in its curved tip position. Thus, the catheter 10 has a blunt forward end that can be manipulated through the intrathecal space.

The practitioner advances the catheter 10 into the intrathecal space, as pictorially shown in FIG. 3. The curved forward ends of both the stylet 12 and the catheter 10 minimize the likelihood that the stylet or catheter would penetrate the substance of the spinal cord. Once the catheter 10 is properly positioned, the practitioner pulls the stylet 12 rearwardly. As the stylet 12 is pulled rearwardly, the tip 20 straightens out to permit removal through the lumen 16 while simultaneously straightening out the distal portion 17 of the intrathecal catheter 10. The practitioner removes the stylet 12 from the catheter 10 while leaving the catheter positioned within in the intrathecal space. The practitioner secures and anchors the intrathecal catheter 10 to adjacent tissue and connects it to the drug delivery pump 13 that is implanted in the patient's abdomen, as pictorially shown in FIG. 4. Those skilled in the art will understand how to tunnel the catheter 10 to the pump and how to connect it thereto using conventional techniques and conventional fittings that are well known. When activated, the pump 13 delivers the medication from its reservoir, through the lumen 16 of the catheter 10, and to the target tissue in the intrathecal space.

Optionally, the tools that the practitioner uses to implant the catheter 10 into the patient can be assembled into a single kit 30. For example, the kit 30 can include a catheter 10 with a stylet 12 having a curved tip 20, a pump 13, a guide needle 32, an insertion device 22, a tunneling tool 36, an anchor (not shown), a sterile drape (not shown), and suturing supplies 34.

While the invention has been described with reference to preferred and example embodiments, it will be understood by those skilled in the art that a variety of modifications, additions and deletions are within the scope of the invention, as defined by the following claims.

What is claimed is:

1. A method for introducing a catheter of an intrathecal drug delivery system into an intrathecal space of a human or animal body, comprising:
providing the intrathecal catheter with an elongate body that is made of a flexible biocompatible material, defines a lumen, and has a proximal portion and a distal portion, the lumen for receiving a stylet and for drug delivery, the distal portion having a closed end and defining at least one lateral opening for drug delivery from the lumen laterally into the intrathecal space, the stylet having a distal tip that is curved in its neutral state, flexible, and stiffer than the distal portion of the intrathecal catheter thereby producing a curve to the distal portion of the catheter when the stylet is fully inserted into the catheter lumen with the stylet distal tip positioned within the catheter distal portion adjacent its closed end, the curved distal portion of the catheter forming a blunt leading portion with a most-forward point along a mid-section of the curve;
inserting the intrathecal catheter, with the stylet housed therein, into an incision in the human or animal body and into the intrathecal space;
guiding the intrathecal catheter, with the stylet housed therein, through the intrathecal space by manipulation of the stylet by advancing the blunt leading portion of the curved distal portion of the intrathecal catheter, with the stylet housed therein, through the intrathecal space;
connecting the proximal portion of the intrathecal catheter to a drug-delivery pump of the intrathecal drug-delivery system; and
removing the stylet from the intrathecal catheter, wherein the curved flexible distal tip of the stylet straightens out during removal from the catheter and at the same time the curved distal portion of the catheter straightens out in the intrathecal space, and wherein upon removal from the catheter the flexible distal tip of the stylet resiliently returns to its neutral curved shape.

2. The method of claim 1, wherein inserting the catheter into the human or animal body and into the intrathecal space further comprises straightening out the catheter distal portion housing the stylet distal tip by inserting the styletted catheter through a guide needle positioned in the intrathecal space, wherein after the distal portion of the catheter is extended out of the guide needle and into the intrathecal space, then the distal portion of the catheter returns to the curved shape under the influence of the curved distal tip of the stylet.

3. The method of claim 1, wherein the curved distal tip of the stylet is J-shaped.

4. A method for introducing a catheter of an intrathecal drug delivery system into an intrathecal space of a human or animal body, comprising:
providing the intrathecal catheter with an elongate body that is made of a flexible biocompatible material, defines a lumen, and has a proximal portion and a distal portion, the lumen for receiving a stylet and for drug delivery, the proximal portion including a fitting, the distal portion having a closed end and defining at least one lateral opening for drug delivery from the lumen laterally into the intrathecal space, the stylet having a distal tip that is curved, in its neutral state, so that a distal end thereof is bent beyond perpendicular relative to a longitudinal axis of a straight section of the stylet, flexible, and stiffer than the distal portion of the intrathecal catheter thereby producing a curve to the distal portion of the catheter when the stylet is fully inserted into the catheter lumen with the stylet distal tip positioned within the catheter distal portion adjacent its closed end, the curved distal portion of the catheter forming a blunt leading portion with a most-forward point along a mid-section of the curve;
inserting the intrathecal catheter, with the stylet housed therein, into an incision in the human or animal body and into the intrathecal space, by straightening out the catheter distal portion housing the stylet distal tip by inserting the styletted catheter through a guide needle positioned in the intrathecal space, wherein after the distal portion of the catheter is extended out of the guide needle and into the intrathecal space, then the distal portion of the catheter returns to the curved shape under the influence of the curved distal tip of the stylet;
guiding the intrathecal catheter, with the stylet housed therein, through the intrathecal space by manipulation of the stylet by advancing the blunt leading portion of the curved distal portion of the intrathecal catheter, with the stylet housed therein, through the intrathecal space;
connecting the proximal portion fitting of the intrathecal catheter to a drug-delivery pump of the intrathecal drug-delivery system; and
removing the stylet from the intrathecal catheter, wherein the curved flexible distal tip of the stylet straightens out during removal from the catheter and at the same time the curved distal portion of the catheter straightens out in the intrathecal space, and wherein upon removal from the catheter the flexible distal tip of the stylet resiliently returns to its neutral curved shape, wherein at no point in the method does the distal tip of the stylet extend distally beyond the closed end of the distal portion of the catheter.

5. The method of claim 4, wherein the curved distal tip of the stylet is J-shaped.

6. The method of claim 4, further comprising implanting the drug-delivery pump of the intrathecal drug-delivery system into the human or animal body.

7. A method for introducing a catheter of an intrathecal drug delivery system into an intrathecal space of a human or animal body, comprising:

providing the intrathecal catheter with an elongate body that is made of a flexible biocompatible material, defines a lumen, and has a proximal portion and a distal portion, the lumen for receiving a stylet and for drug delivery, the proximal portion including a fitting, the distal portion having a closed end and defining at least one lateral opening for drug delivery from the lumen laterally into the intrathecal space, the stylet having a distal tip that is curved in a "J" shape in its neutral state, flexible, and stiffer than the distal portion of the intrathecal catheter thereby producing a J-shaped curve to the distal portion of the catheter when the stylet is fully inserted into the catheter lumen with the stylet distal tip positioned within the catheter distal portion adjacent its closed end, the curved distal portion of the catheter forming a blunt leading portion with a most-forward point along a midsection of the curve;

inserting the intrathecal catheter, with the stylet housed therein, into an incision in the human or animal body and into the intrathecal space, by straightening out the catheter distal portion housing the stylet distal tip by inserting the styletted catheter through a guide needle positioned in the intrathecal space, wherein after the distal portion of the catheter is extended out of the guide needle and into the intrathecal space, then the distal portion of the catheter returns to the curved shape under the influence of the curved distal tip of the stylet;

guiding the intrathecal catheter, with the stylet housed therein, through the intrathecal space by manipulation of the stylet by advancing the blunt leading portion of the curved distal portion of the intrathecal catheter, with the stylet housed therein, through the intrathecal space;

implanting a drug-delivery pump of the intrathecal drug-delivery system into the human or animal body;

connecting the proximal portion fitting of the intrathecal catheter to the drug-delivery pump of the intrathecal drug-delivery system; and removing the stylet from the intrathecal catheter, wherein the curved flexible distal tip of the stylet straightens out during removal from the catheter and at the same time the curved distal portion of the catheter straightens out in the intrathecal space, and wherein upon removal from the catheter the flexible distal tip of the stylet resiliently returns to its neutral curved shape, wherein at no point in the method does the distal tip of the stylet extend distally beyond the closed end of the distal portion of the catheter.

* * * * *